(12) United States Patent
Ono et al.

(10) Patent No.: US 8,187,624 B1
(45) Date of Patent: May 29, 2012

(54) COMPOSITIONS FOR TAKING DIETARY FIBERS

(75) Inventors: Shigeyuki Ono, Tokyo (JP); Yasushi Kajihara, Tokyo (JP); Yoko Sugiura, Tokyo (JP); Hiroyuki Sugaya, Tokyo (JP)

(73) Assignee: Kao Corporation, Tokyo (JP)

( * ) Notice: Subject to any disclaimer, the term of this patent is extended or adjusted under 35 U.S.C. 154(b) by 265 days.

(21) Appl. No.: 10/297,582

(22) PCT Filed: Jun. 14, 2000

(86) PCT No.: PCT/JP00/03850
§ 371 (c)(1), (2), (4) Date: Dec. 12, 2002

(87) PCT Pub. No.: WO01/95746
PCT Pub. Date: Dec. 20, 2001

(51) Int. Cl.
*A61K 47/00* (2006.01)
*A23L 1/50* (2006.01)
*A23L 2/00* (2006.01)
*A61N 65/00* (2006.01)

(52) U.S. Cl. ......... 424/439; 426/573; 426/590; 424/750

(58) Field of Classification Search .................. 424/439, 424/434, 435
See application file for complete search history.

(56) References Cited

U.S. PATENT DOCUMENTS

| | | | |
|---|---|---|---|
| 5,085,883 A | | 2/1992 | Garleb et al. |
| 5,104,677 A | * | 4/1992 | Behr et al. .................... 426/590 |
| 5,112,964 A | * | 5/1992 | Aoe et al. ........................ 536/56 |
| 5,126,143 A | * | 6/1992 | Nakashima et al. .......... 424/439 |
| 5,622,738 A | * | 4/1997 | Takeuchi et al. ................ 426/52 |
| 5,629,036 A | * | 5/1997 | Yanetani et al. ................ 426/19 |
| 6,004,610 A | * | 12/1999 | Wang et al. ................... 426/599 |
| 6,017,550 A | * | 1/2000 | Berk et al. .................... 424/401 |

FOREIGN PATENT DOCUMENTS

| | | |
|---|---|---|
| EP | 552728 | 7/1993 |
| EP | 1 125 507 | 8/2001 |
| JP | 62-220169 | 9/1987 |
| JP | 02-276556 | 11/1990 |
| JP | 7-12294 | 2/1995 |
| JP | 09-065855 | 3/1997 |
| JP | 11-75777 | 3/1999 |
| JP | 11075777 A * | 3/1999 |
| JP | 11-225706 | 8/1999 |
| JP | 11-253114 | 9/1999 |
| JP | 11-302448 | 11/1999 |
| JP | 2000-232855 | 8/2000 |
| WO | WO 9904027 A1 * | 1/1999 |

OTHER PUBLICATIONS

Nishizawa et al. "Effect of Depolymerized Sodium Alginate on the Serum and Liver Cholesterol Levels in Cholesterol-Fed Rats", J.Home Econ. Jpn. vol. 48 No. 8 695-698 (1997).*
Takahashi et al., Effect of partially hydrolyzed guar gum on fecal output in human volunteers, vol. 13, Issue 6, Jun. 1993, p. 649-657.*
T. Kondo, et al., Journal of Gastroenterology, vol. 31, pp. 654-658, XP-009024681, "Breath Hydrogen and Methane Excretion Produced by Commercial Beverages Containing Dietary Fiber", 1996.
G. D. Sunvold, et al., Journal of Animal Science, vol. 73, No. 4, pp. 1100-1109, XP-002072351, "Dietary Fiber for Dogs: In Vitro Fermentation of Selected Fiber Sources for Dog Fecal Inoculum and in Vivo Digestion and Metabolism of Fiber-Supplement Diets", 1995.
*Biosci. Biotechnol. Biocheem.*, 63 (8)m 1340-1345, 1999.
Japan Food Research Laboratories No. 30 Dec. 2002 w. partial English language translation.
Food & Beverage Asia, Aug. 2004—Prebiotics.

* cited by examiner

*Primary Examiner* — Michael G Hartley
*Assistant Examiner* — Nabila Ebrahim
(74) *Attorney, Agent, or Firm* — Oblon, Spivak, McClelland, Maier & Neustadt, L.L.P.

(57) ABSTRACT

The invention relates to a composition for taking dietary fibers, which comprises 1 to 50% by weight, on the basis of the whole composition, of dietary fibers composed of water-soluble and hardly fermentable dietary fiber and water-soluble and fermentable dietary fiber, wherein the water-soluble and fermentable dietary fiber is contained in a proportion of 0.1 to 3 parts by weight per part by weight of the water-soluble and hardly fermentable dietary fiber. The composition remarkably ameliorates not only bowel movement frequency but also full consciousness, feeling of unsatisfied defecation, etc. and is hence useful as food for ameliorating bowel movement.

7 Claims, No Drawings

COMPOSITIONS FOR TAKING DIETARY FIBERS

TECHNICAL FIELD

The present invention relates to a composition for taking dietary fibers useful as a food for ameliorating bowel movement.

BACKGROUND ART

The functions of dietary fibers are roughly said to be formation of a feces skeleton by water holding ability and a source of energy supply to enteric canals by short-chain fatty acids formed by being used in enterobacteria, and the details and degrees of the functions are not always homogeneous in the respective dietary fibers. Accordingly, it is recommended to take various dietary fibers from various foods. However, it is difficult to take various dietary fibers different in the details and degrees of the functions with good balance in an actual dietary life, and there is a demand for proposal of dietary fiber foods which can effectively support the action of the large bowel.

As a food for ameliorating bowel movement, which incorporates a plurality of dietary fibers, has been known that incorporating hardly water-soluble dietary fiber and water-soluble dietary fiber (Japanese Patent Publication No. 12294/1995). The hardly water-soluble dietary fiber composed mainly of cellulose is partially fermented by enterobacteria to expose a water-soluble structure or water-soluble component contained in the dietary fiber, thereby increasing water holding ability to contribute to the formation of the feces skeleton. However, it is easy to be affected by fermentable dietary fiber coexisting at the same time, and so the intended water holding ability cannot be always developed, and the water holding ability for the formation of the feces skeleton by the dietary fiber composed mainly of cellulose is hard to be said to be sufficient because of its partial gelling in the vicinity of hardly fermentable dietary fiber. In addition, in the form of a drink which is considered to be easiest to be taken, disadvantages are encountered from the viewpoint of incorporation when hardly water-soluble dietary fiber is contained as a component.

DISCLOSURE OF THE INVENTION

The present inventors have paid attention to complete separation of the function of dietary fiber forming the skeleton of feces by the water holding ability from the function of dietary fiber which is fermented by enterobacteria to form short-chain fatty acids which will become an energy source for enteric canals, and water-soluble dietary fibers applicable to the form of drink easy to be taken. More specifically, since the formation of the feces skeleton is fundamentally based on the water holding capacity by gelling, two kinds of dietary fibers of water-soluble and hardly fermentable dietary fiber which is not fermented by enterobacteria and can effectively develop the water holding capacity even in the large bowel, and water-soluble and fermentable dietary fiber which is fermented by the enterobacteria to form short-chain fatty acids which are an energy source for enteric canals have been determined to be used. It has been found that when these 2 dietary fibers are combined in certain proportions, the water-soluble and hardly fermentable dietary fiber exhibits an effective feces bulk-increasing effect by the water holding ability thereof to impart physical stimulation to the enteric canals, and the water-soluble and fermentable dietary fiber is used by the enterobacteria to form short-chain fatty acids to impart chemical stimulation to the enteric canals, thereby facilitating the peristaltic movement of the enteric canals from both sides to achieve a high ameliorating effect on bowel movement.

The present invention provides a composition for taking dietary fibers, which comprises 1 to 50% by weight, on the basis of the whole composition, of dietary fibers composed of water-soluble and hardly fermentable dietary fiber and water-soluble and fermentable dietary fiber, wherein the water-soluble and fermentable dietary fiber is contained in a proportion of 0.1 to 3 parts by weight per part by weight of the water-soluble and hardly fermentable dietary fiber.

BEST MODE FOR CARRYING OUT THE INVENTION

Examples of the water-soluble and hardly fermentable dietary fiber used in the composition according to the present invention include sodium alginate, depolymerized sodium alginate, carrageenan, fucoidan, laminaran, sodium carboxymethyl cellulose, polydextrose, and agar. Among these depolymerized sodium alginate and polydextrose are particularly preferred in that the viscosities of aqueous solutions thereof are low.

Examples of the water-soluble and fermentable dietary fiber include pectin, dopolymerized pectin, guar gum, molecular weight-reduced guar gum, hemicellulose, gum arabic, glucomonnan, locust bean gum, pullulan, curdlan, xanthan gum, gellan gum and indigestible dextrin. Among these, depolymerized pectin, depolymerized guar gum, hemicellulose, gum arabic, pullulan and indigestible dextrin are particularly preferred in that the viscosities of aqueous solutions thereof are low. As hemicellulose, may be used those derived from wheat, soybean and corn. However, that derived from corn is preferred because offensive taste and odor caused by the raw material are little. In addition, impurities such as saponin are scarcely mixed, and problems upon preparation, such as foaming, are also scarcely caused. Such hemicellulose is hence preferred. Further, hemicellulose having a low molecular weight, particularly, adjusted in its average molecular weight to 100,000 or lower is preferred because the viscosity of an aqueous solution thereof is low. In order to adjust the average molecular weight of hemicellulose to 100,000 or lower, it is only necessary to cause an enzyme to act on high-molecular weight hemicellulose or subject the high-molecular weight hemicellulose to thermal decomposition or decomposition under pressure in accordance with a method known per se in the art.

These dietary fibers preferably have a viscosity of 20 mPa·s or lower in terms of a 5% by weight of an aqueous solution at room temperature when they are used in drink.

The composition according to the present invention contains 1 to 50% by weight, preferably 2 to 20% by weight, particularly preferably 5 to 10% by weight of dietary fibers composed of the water-soluble and hardly fermentable dietary fiber and the water-soluble and fermentable dietary fiber from the viewpoints of an ameliorating effect on bowel movement and an improving effect on intestinal disorder.

In the dietary fibers, the water-soluble and fermentable dietary fiber is contained in a proportion of 0.1 to 3 parts by weight (preferably 0.3 to 3 parts by weight, particularly preferably 0.5 to 2 parts by weight) per part by weight of the water-soluble and hardly fermentable dietary fiber from the viewpoints of the ameliorating effect on bowel movement and the improving effect on intestinal disorder.

The short-chain fatty acids formed from the fermentable dietary fiber participate in increase of water content in feces and also contribute to imparting of softness to the feces. When the proportion of the water-soluble and fermentable dietary fiber to the water-soluble and hardly fermentable dietary fiber exceeds 3 times by weight, the proportion of the short-chain fatty acids formed is increased compared with the water-soluble and hardly fermentable dietary fiber forming the feces skeleton by the water-retaining ability to bring about formation of a loose passage in some cases. It is hence not preferable to contain the water-soluble and fermentable dietary fiber in such a high proportion. Since the short-chain fatty acids formed are neutralized in the large bowel to generate carbon dioxide, a feeling of displeasure such as full consciousness is easy to occur when the proportion of the water-soluble and fermentable dietary fiber is higher. Such a high proportion is also not preferable from such a point of view.

No particular limitation is imposed on the form of the composition according to the present invention so far at the form is such that the dietary fibers can be orally taken, and it can be provided as food such as functional food, health food or snack food, a drug, or the like. Examples of the form of food include cookie, flake, wafer, tablets, granules and snack confectionery, and besides drink, with the form of drink being particularly preferred from the viewpoint of easy intake.

In order to provide the composition according to the present invention in the form of food, other dietary fibers, for example, starch and dextrin; saccharides such as sucrose; proteins such as casein, soybean protein and albumen; minerals such as calcium carbonate and iron lactate; vitamins such as vitamins A, $B_1$, $B_2$, $B_{12}$ and C; and rice, barley, wheat, corn, various kinds of vegetables, meats, edible oils, seasonings, water and the like may be suitably incorporated either singly or in any combination thereof in addition to the 2 dietary fibers.

The amount of the composition according to the present invention to be taken is preferably 1 to 20 g in terms of the amount of the dietary fibers per time (meal).

EXAMPLES

Examples 1 and 2

Preparation Method of Test Food

Cookies of their corresponding formulations shown in Table 1 were prepared in accordance with a method known per se in the art to be provided as test food. A cookie dough before baking is divided into individual cookie portions (each 10 g), and 3 baked products thereof are taken, whereby the following amounts of test dietary fibers required per day to be aimed at can be satisfied.
(Amounts of Test Dietary Fibers Required Per Day)
Water-soluble and hardly fermentable dietary fiber . . . 3 g
Water-soluble and fermentable dietary fiber . . . 3 g

TABLE 1

| Material | Amount incorporated |
| --- | --- |
| Salt-free butter | 50 g |
| Wheat flour (Soft flour) | 50 g |
| Water-soluble and hardly fermentable dietary fiber | 25 g |
| Water-soluble and fermentable dietary fiber | 25 g |
| Sugar (granulated sugar) | 50 g |
| Egg (whole egg) | 40 g |
| Albumen | 10 g |

TABLE 1-continued

| Material | Amount incorporated |
| --- | --- |
| Sodium bicarbonate | 1 g |
| Ammonium carbonate | 2 g |

[Testing Method]

With respect to subjects conscious of constipation or tendency of constipation, non-ingestion period was taken for 7 days, and ingestion period was successively taken for 7 days. After completion of the ingestion period, the conditions of bowel movement during the ingestion period had been taken were compared with the conditions of bowel movement during the non-ingestion period had been taken by the following questionnaire.
(1) Improving effect on bowel movement frequency: research on improvement in bowel movement frequency
  (Improved; Increased; Unchanged; Neither increased nor decreased; Deteriorated; Decreased)
(2) Change in condition of bowels: Overall evaluation including factors of a feeling of displeasure such as full consciousness or feeling of unsatisfied defecation in addition to bowel movement frequency
  (Became better; Improved; Unchanged; Became worse; Deteriorated)

Example 1

Water-soluble and hardly fermentable dietary fiber . . . Depolymerized sodium alginate (viscosity of a 5% by weight aqueous solution=about 10 mPa·s)
Water-soluble and fermentable dietary fiber . . . Depolymerized guar gum (viscosity of a 5% by weight aqueous solution=about 5 mPa·s)

Example 2

Water-soluble and hardly fermentable dietary fiber . . . Depolymerized sodium alginate (the same as that used in Example 1)
Water-soluble and fermentable dietary fiber . . . Hemicellulose (viscosity of a 5% by weight aqueous solution=about 16 mPa·s)

Comparative Example 1

Hardly water-soluble dietary fiber was used in place of the water-soluble and hardly fermentable dietary fiber.
Hardly water-soluble dietary fiber . . . Cabbage dietary fiber
Water-soluble and fermentable dietary food . . . Depolymerized guar gum (the same as that used in Example 1)
The results are shown in Table 2.

TABLE 2

|  |  | Improving effect on bowel movement frequency | Change in condition of bowels |
| --- | --- | --- | --- |
| Comp. Ex. 1 | Case improved | 4/8 persons | 1/8 persons |
|  | Unchanged | 2/8 persons | 4/8 persons |
|  | Case deteriorated | 2/8 persons | 3/8 persons |
| Ex. 1 | Case improved | 5/9 persons | 3/9 persons |
|  | Unchanged | 1/9 persons | 6/9 persons |
|  | Case deteriorated | 3/9 persons | 0/9 persons |

TABLE 2-continued

|  |  | Improving effect on bowel movement frequency | Change in condition of bowels |
|---|---|---|---|
| Ex. 2 | Case improved | 8/10 persons | 7/10 persons |
|  | Unchanged | 0/10 persons | 2/10 persons |
|  | Case deteriorated | 2/10 persons | 1/10 persons |

As apparent from the results shown in Table 2, it is understood that the compositions according to the present invention with the water-soluble and hardly fermentable dietary fiber and the water-soluble and fermentable dietary fiber combined in specified proportions is far excellent not only in the improving effect on bowel movement frequency but also in the improving effect on the feeling of displeasure such as full consciousness or feeling of unsatisfied defecation compared with the food incorporating another dietary fiber.

Example 3

The following components were mixed and sterilized, thereby preparing a composition according to the present invention in the form of drink.

| (Component) | (% by weight) |
|---|---|
| Depolymerized sodium alginate (the same as that used in Example 1) | 2.5 |
| Indigestible dextrin (viscosity of a 5% by weight aqueous solution = about 3 mPa · s) | 2.5 |
| high fructose syrup from glucose-fructose mixture | 5.0 |
| Citric acid | 0.1 |
| Grapefruit juice | 20.0 |
| Flavor | 0.1 |
| Water | 68.8 |

Comparative Example 2

Sodium alginate and indigestible dextrin were used in a mixing ratio (1:9) described in Example 2 of Japanese Patent No. 2779616 to prepare a drink similar to that of Example 3 described above.

| (Component) | (% by weight) |
|---|---|
| Depolymerized sodium alginate (the same as that used in Example 1) | 0.5 |
| Indigestible dextrin (the same as that used in Example 3) | 4.5 |
| High fructose syrup from glucose-fructose mixture | 5.0 |
| Citric acid | 0.1 |
| Grapefruit juice | 20.0 |
| Flavor | 0.1 |
| Water | 68.8 |

Test Example 2

The drink according to Example 3 and the drink according to Comparative Example 2 were used to conduct a comparative investigation.
Test drinks: Drinks of Example 3 and Comparative Example 2 (100 mL/day).
Testing method: With respect to subjects conscious of constipation or tendency of constipation, non-ingestion period was taken for 7 days, and ingestion period was successively taken for 7 days. After completion of the ingestion period, the conditions of bowel movement during the ingestion period had been taken were compared with the conditions of bowel movement during the non-ingestion period had been taken in the same manner as described above.

The results are shown in Table 3.

TABLE 3

|  |  | Improving effect on bowel movement frequency | Change in condition of bowels |
|---|---|---|---|
| Ex. 2 | Case improved | 8/12 persons | 8/12 persons |
|  | Unchanged | 3/12 persons | 3/12 persons |
|  | Case deteriorated | 1/12 persons | 1/12 persons |
| Comp. Ex. 1 | Case improved | 5/11 persons | 4/11 persons |
|  | Unchanged | 6/11 persons | 6/11 persons |
|  | Case deteriorated | 0/11 persons | 1/11 persons |

As apparent from the results shown in Table 3, it is understood that the drink with the water-soluble and hardly fermentable dietary fiber and the water-soluble and fermentable dietary fiber incorporated in a range (1:0.1 to 1:3) according to the present invention is far excellent compared with the drink in which the range thereof is 1:9.

Example 4

A drink was prepared according to a formulation shown below.

The drink (100 mL) is taken, whereby the amounts of dietary fibers required per day to be aimed at can be satisfied.

| (Component) | (% by weight) |
|---|---|
| Depolymerized sodium alginate (the same as that used in Example 1) | 4 |
| Depolymerized guar gum (the same as that used in Example 1) | 5 |
| Reducing maltose syrup | 3 |
| Erythritol | 6 |
| Flavor | 0.2 |
| Citric acid | 0.3 |
| Water | Balance |
|  | 100 (100 mL) |

Example 5

A drink was prepared according to a formulation shown below.

The drink (100 mL) is taken, whereby the amounts of dietary fibers required per day to be aimed at can be satisfied.

| (Component) | (% by weight) |
|---|---|
| Depolymerized sodium alginate (the same as that used in Example 1) | 4 |
| Depolymerized hemicellulose (viscosity of a 5% by weight aqueous solution = about 7 mPa · s) | 5 |

-continued

| (Component) | (% by weight) |
|---|---|
| Reducing maltose syrup | 3 |
| Erythritol | 6 |
| Flavor | 0.2 |
| Citric acid | 0.3 |
| Water | Balance |
| | 100 (100 mL) |

INDUSTRIAL APPLICABILITY

Since the compositions according to the present invention incorporate water-soluble and hardly fermentable dietary fiber contributing to the formation of feces skeleton and water-soluble and fermentable dietary fiber fermented by enterobacteria to form short-chain fatty acids which are an energy source mainly for the large bowel are incorporated in combination, not only bowel movement frequency but also full consciousness, feeling of unsatisfied defecation, etc. are remarkably ameliorated. Thus, the compositions are useful as foods for ameliorating bowel movement.

The invention claimed is:

1. A drink, which comprises 2 to 20% by weight of water-soluble dietary fibers, on the basis of the drink, said water-soluble dietary fibers being composed of water-soluble and hardly fermentable dietary fiber and water-soluble and fermentable dietary fiber,
wherein said water-soluble and fermentable dietary fiber is present in a proportion of 0.1 to 3 parts by weight per part by weight of the water-soluble and hardly fermentable dietary fiber,
wherein said water-soluble and hardly fermentable dietary fiber comprises depolymerized sodium alginate, and
wherein said water-soluble and fermentable dietary fiber is at least one selected from the group consisting of indigestible dextrin, molecular weight-reduced guar gum and depolymerized hemicellulose,
wherein a 5% by weight aqueous solution at room temperature of said water-soluble and hardly fermentable dietary fiber has a viscosity of 20 mPa·s or lower, and a 5% by weight aqueous solution at room temperature of said water-soluble and fermentable dietary fiber has a viscosity of 20 mPa·s or lower.

2. The drink according to claim 1, which is a drink for ameliorating bowel movement.

3. The drink of claim 1, wherein said drink comprises 5 to 10% by weight of water-soluble dietary fibers.

4. The drink of claim 1, wherein said water-soluble and fermentable dietary fiber is contained in a proportion of 0.3 to 3 parts by weight.

5. The drink of claim 1, wherein said water-soluble and fermentable dietary fiber comprises indigestible dextrin.

6. The drink of claim 1, wherein said water-soluble and fermentable dietary fiber comprises molecular weight-reduced guar gum.

7. The drink of claim 1, wherein said water-soluble and fermentable dietary fiber comprises depolymerized hemicellulose.

\* \* \* \* \*